United States Patent [19]

Idelsohn et al.

[11] 4,207,472
[45] Jun. 10, 1980

[54] LUMBER INSPECTION AND OPTIMIZATION SYSTEM

[75] Inventors: Jerome M. Idelsohn; Paul A. Mueller, both of Detroit; M. David Freedman, Southfield, all of Mich.; Raymond T. Hebert, Saratoga; Edward A. King, Orinda, both of Calif.

[73] Assignee: The Bendix Corporation, Southfield, Mich.

[21] Appl. No.: 933,393

[22] Filed: Aug. 14, 1978

Related U.S. Application Data

[60] Division of Ser. No. 818,252, Jul. 22, 1977, Pat. No. 4,149,089, which is a continuation of Ser. No. 638,116, Dec. 5, 1975, abandoned.

[51] Int. Cl.$^2$ .......................................... G01N 21/32
[52] U.S. Cl. ................................. 250/563; 144/312
[58] Field of Search ............... 290/560, 562, 563, 572; 356/379, 380, 397, 398; 144/312

[56] References Cited

U.S. PATENT DOCUMENTS

| | | | |
|---|---|---|---|
| 3,120,861 | 2/1964 | Finlay et al. | |
| 3,260,851 | 7/1966 | Jacobsson | |
| 3,329,181 | 7/1967 | Buss et al. | |
| 3,389,789 | 6/1968 | Watson et al. | |
| 3,410,643 | 11/1968 | Jorgensen | |
| 3,490,147 | 1/1970 | Brichard et al. | |
| 3,490,320 | 1/1970 | Valembois | |
| 3,760,667 | 9/1973 | Maxey et al. | |
| 3,897,156 | 7/1975 | Chasson | 144/312 |
| 3,983,403 | 9/1976 | Dahlstrom | 250/560 |
| 4,149,089 | 4/1979 | Idelsohn et al. | 250/563 |

OTHER PUBLICATIONS

"Programming for Lumberyield," by G. H. Englerth et al., Forest Products Journal, vol. 16, No. 7, Sep. 1966.
"Tomorrow: Computer Made Sawing Decisions?", by H. Hallock et al., Forest Prod. Jour., vol. 20, No. 9, Sep. 1970.
"Optimum Sequence of Cutting Bills," by W. L. Hafley et al., Forest Prod. Jour., vol. 223, No. 8, Aug. 1973.

Primary Examiner—David C. Nelms
Attorney, Agent, or Firm—James R. Ignatowski; Russel C. Wells

[57] ABSTRACT

A lumber inspection and optimization system is disclosed combining the speed of electro-optic scanning for flaw detection with electronic data manipulation and computation for optimizing the utilization of the lumber in accordance with an order entry list specifying the dimensions, grade and priority of boards desired to cut from each piece of lumber inspected by the system. The system receives input data from an order entry device and an electro-optical scanner. The digital scan data from the electro-optical scanner is electronically processed to form a flaw data buffer containing the edge location of all the detected flaws enlarged to compensate for defective material usually surrounding each flaw. Optimization of the material is accomplished by electronically comparing the order entry data with the location of the flaws in the flaw buffer to generate cut line data indicative of where the board is to be cut. The cut line data may be used to either actuate a saw to cut the lumber at the locations specified by the cut line data or actuate a marker to mark the lumber at the specified locations. When the order entry data includes pieces having permitted defects, the disclosed system includes a defect classification input device permitting a human inspector to insert defect classification data into the flaw data buffer prior to optimization. The preferred embodiment utilizes a mini computer programmed to process the flaw data, optimize the utilization of the board inspected and generate the cut line data.

14 Claims, 17 Drawing Figures

SPECIAL END OF FRAME AND END OF BOARD FORMATS

LUMBER INSPECTION AND OPTIMIZATION SYSTEM

This is a division, of application Ser. No. 818,252, filed July 22, 1977 U.S. Pat. No. 4,149,089 which is a continuation of Application Ser. No. 638,116, filed Dec. 5, 1975, now abandoned.

BACKGROUND OF THE INVENTION

1. Field of the Invention

The present invention is generally directed to systems maximizing the utilization of materials having irregular and unpredictable flaws and defects such as found in forest products, plate glass, sheet metal and the like. The invention is particularly directed to a lumber inspection and optimization system embodying an electro-optical scanner generating data indicative of the location and size of flaws, a man-operated flaw classification device generating data indicative of the flaw class, an order entry device generating data indicative of the size and shape of the desired pieces, and an electronic processor generating data indicative of the locations where the inspected piece of lumber is to be cut for maximum yield.

2. Prior Art

The woodworking industries, such as the furniture, millwork and molding plants, are faced with maximizing the utilization of the available lumber. The requirements of the various woodworking industries vary over a considerable range dependent primarily upon the principle output or product. The requirements range from clear, flaw-free board pieces to pieces which may contain certain classes of imperfections of given sizes of other types of pieces where certain classes of imperfections, such as tight knots, are even desirable. An example of the latter are knotty pine panels. Further, each woodworking plant has requirements for a variety of sizes of board pieces to meet production requirements. The various board pieces must be cut from larger boards which come to the plant or factory as unfinished boards. These boards inherently possess various classes of defects and imperfections of different sizes, such as tight and loose knots, cracks, checks, splits, bark, stain, pitch pockets and the like. The problem facing each woodworking facility is the analysis of each incoming board to determine how it may be cut to most efficiently meet the production requirements of the particular plant of facility. Typically, this is done by an experienced human inspector who, having knowledge of the size and quality of board pieces required to meet the facility's production need, evaluates each board and makes an on-the-spot determination as to the most efficient way to cut the particular board. This method has limitations particularly when the board is relatively large. Under these conditions the inspector does not get a good overall perspective of the whole board and his evaluation of each board takes place section by section. Production requirements further limit the time the human inspector has to inspect each board. Therefore, his optimization of any given board may be less than desired. Because of these factors, optimization by a human inspector is generally considered to be inefficient and not cost effective.

To overcome this deficiency, the prior art has disclosed a variety of systems to aid or replace the human inspector in identifying and evaluating flaws in forest products. Finlay et al in U.S. Pat. No. 3,120,861—"Method and Apparatus for Identifying and Evaluating Surface Characteristics of Forest Products" (Feb. 11, 1964) discloses a rudimentary system for identifying and evaluating surface characteristics of forest products. The Finlay et al system electro-optically scans the surface of the board to detect the flaws and then either marks the board where it is to be cut or actuates a saw to remove these flaws. This system only locates the flaws along the length axis of the board. Detection of objectionable flaws in the Finlay et al system is determined by the pulse amplitude of the detected flaw and a recurrence on at least three successive scans. A deficiency of this system is that some flaws are difficult to detect by scanning the surface and may go undetected while surface dirt or other surface characteristics, such as an unusually dark grain, may be detected as a flaw resulting in a waste of material.

The concept of utilizing a computer for optimizing the cutting of lumber is introduced by Buss et al in U.S. Pat. No. 3,329,181—"Apparatus and Method for Cutting Assorted Length from Material Having Irregular and Random Defects" (July 4, 1967). In the Buss et al system the flaws are manually located by an inspector using an electro-mechanical scanner which generates electrical signals compatible with a computer indicative of the flaw's location. The inspector locates the flaw and marks the coordinates of the upper right-hand corner and lower left-hand corner of an imaginary rectangle encompassing the flaw. The inspector's control also contains a button whereby he may indicate that the indicated flaw is useable in certain inferior grades of stock needed by the plant or facility. The computer stores the size, location and class of defect selected by the inspector and then, in accordance with a predetermined program, determines how the board should be cut for optimum utilization of each board. The computer program contains the size and grade of the board pieces required, as well as the number of each kind of piece necessary to meet its production requirements. Each board piece is weighed in the computation processes according to any of several parameters, such as the monetary value of the particular size and grade, a priority based on the difficulty of obtaining the specific size and grade, as well as the number of pieces required. In addition to determining how the board should be cut, the computer remembers the number of pieces of each kind yielded by that particular board. This information provides an inventory check and also can be input back into the computer program to readjust the arbitrary priority of each type of board to keep the output relatively balanced. Computer programs to perform this type of function are well known in the art. Brichard et al in U.S. Pat. No. 3,490,147—"Method for Optimally Cutting Successive Panels in Pieces from a Sheet or Strip" (Jan. 20, 1970) and Valembois et al in U.S. Pat. No. 3,490,320 "Method for Obtaining Patterns for Cutting Pieces Out of Sheets or Strips" (Jan. 20, 1970), as well as Buss, teach using computers for optimizing the cutting of sheets or strips in accordance with predetermined programs wherein the various sizes and grades have weighted values. The concept for using a computer for optimizing the cutting of lumber for maximum yield is also found in published literature. Typical examples are Englerth and Dummire—"Programming for Lumber Yield", *Forest Products Journal*, Vol. 16, No. 9, Sept. 1966—Hallock and Bulgrin, "Tomorrow: Computer Made Sawing Decisions", *Forest Products Journal*, Vol. 20, No. 9, Sept. 1970—Hafley and Hanson, "Optimum Sequence of Cutting Bills", *Forest Products Journal,* Vol. 23, No. 8, Aug. 1973. These computer programs can be adjusted for maximum monetary yield, maximum useable lumber or maximum yield for specific sizes in predetermined proportions.

The problems of the prior art systems include flaw detection and classification, as well as imparting the required information to the computer in a fast and efficient manner. The disclosed system combines the judgment capabilities of a human inspector with the speed of an electro-optical scanner in a manner to provide the proper information to the computer in a useable form in the most efficient manner.

SUMMARY OF THE INVENTION

The invention is a lumber inspection and optimization system combining the speed of electro-optic scanning for flaw detection and location with a computer for determining the optimum way a board is to be cut for maximum yield per dollar value, lumber utilization, and/or to fulfill the production requirements of a woodworking plant. The system may either mark the board at computer determined cut line locations or may embody a computer actuated saw to cut the board at the determined locations. The preferred embodiment of the system includes an upstream inspector station, an electro-optical scanner, a flaw processor, a lumber optimization computer, an order entry device and an output station. At the inspector station a human inspector may enhance a flaw for positive detection by the electro-optical scanner or may suppress surface markings or other unobjectionable characteristics which the electro-optical scanner would detect as an objectionable flaw. The electro-optical scanner scans opposite sides of the board in a sequentially interlaced scanning pattern to generate scan data indicative of the surface characteristics and the precise location of the flaws on both sides of the board. The electro-optical scanner includes an optical scanner, a data quantizer and a scanner interface to format the scan data into a format acceptable to the computer. The flaw processor receives flaw data from the electro-optical scanner, generates enlarged rectangles about each detected flaw to compensate for defective areas usually surrounding each flaw and then stores the location of edges of the enlarged rectangles in a flaw data buffer. If the order entry includes pieces of lumber which may have predetermined classes of defects, the Inspector Station further includes a defect classification device operated by the human inspector which generates data indicative of the approximate location and class of each flaw. This flaw class is subsequently combined with the scan data in the flaw processor and stored in the flaw data buffer. The lumber optimization computer compares the data in the flaw data buffer with the data received from the order entry device and computes, in accordance with a predetermined program, the optimum way in which the board is to be cut. The order entry device enters into the computer the size, priority and classes of permitted flaws for each different piece desired for a particular run, day and/or facility. The output station receives the data from the lumber optimizer computer and either marks the lumber at the locations where it is to be cut or actuates a saw to cut the lumber, as determined by the lumber optimizer computer.

The object of the invention is a lumber inspection and optimization system utilizing the speed and accuracy of electro-optical scanning in combination with inputs from a human inspector to locate and classify the flaws and to optimize the cutting of the lumber in accordance with predetermined board requirements using a mini computer. Another object of the invention is a system in which both sides of the board are simultaneously scanned and the scan data is quantized to permit rapid and accurate determination of the defects, their type and location. These and other objects will become evident from the accompanying drawings, a reading of the specification and claims.

BRIEF DESCRIPTION OF THE PREFERRED EMBODIMENT

Figure 1:
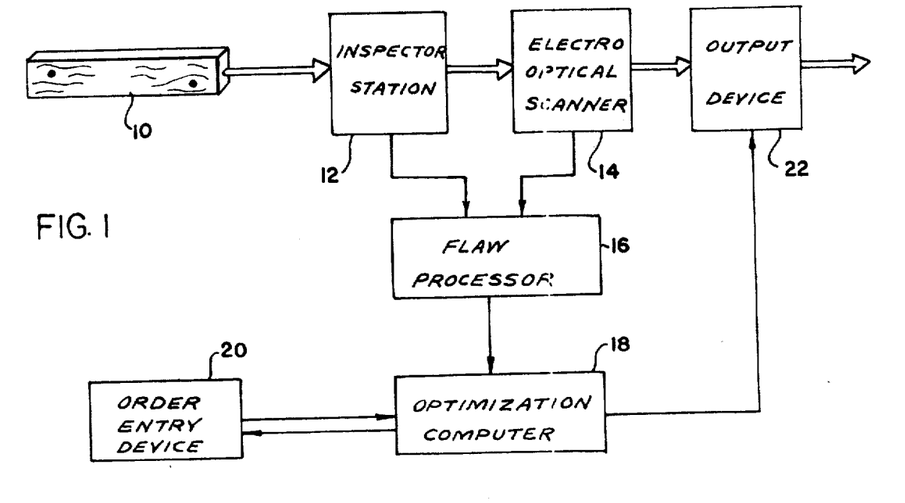
FIG. 1 is a block diagram illustrating the basic elements of the disclosed lumber inspection and optimization system.

A block diagram of the disclosed lumber inspection and optimization system is shown in FIG. 1. The broad arrows show the path of an incoming piece of lumber illustrated as board 10 through the inspection and optimizer system while the narrow lines show the data flow through the system. The lumber inspection and optimizer system comprise an Inspector Station 12, an Electro-Optical Scanner 14, a Flaw Processor 16 and the Lumber Optimization Computer 18 and Order Entry Device 20 and an Output Device 22. The board 10, by means of a conveyor (not shown) first passes through an Inspector Station 12 where it is inspected by a human inspector who enhances difficult to detect flaws and suppresses surface characteristics which may erroneously be detected by the Electro-Optical Scanner 14 as flaws. The Inspector Station 12 may also embody a defect classification input control which permits the human inspector to classify certain visible flaws. This latter information, when available, is transformed to electrical data and stored in the Flaw Processor 16 in the same sequence as detected by the Electro-Optical Scanner 14. After passing through the Inspector Station, the board 10 passes through the Electro-Optical Scanner 14 which electro-optically scans both sides of the board and generates scan data indicative of the size of the board, as well as the size, shape and exact location of the flaws. The flaw class data from the Inspector Station and the scan data are processed in the Flaw Processor 16 to generate flaw data which is indicative of the size, the class and the exact location of each flaw. The Flaw Processor also forms enlarged rectangles about each detected flaw in accordance with fixed rules to include in the detected flaw area cross grain and other objectional defects which typically accompany the flaws.

Phyiscal descriptions of pieces required for production or needed to fill sales orders are entered into the Order Entry Device 20. The physical description of each piece will normally include its size, class of defects allowed when certain classes of defects are permitted, the value and the priority of each piece. The Order Entry Device 20 may be a tape or card reader, a keyboard or any other device capable of transforming an input order into electrical signals compatible with the language of the Optimization Computer.

Hereinafter, the term "board" will refer to the rough piece of lumber input into the lumber inspection and optimizing system and "pieces" will refer to the sub-parts cut from the board. Data from the Order Entry Device 20 along with the flaw data from the Flaw Processor 16 are input into the Lumber Optimization Computer 18 where the utilization of the lumber in the board is maximized in accordance with the flaw data, the order entry data and the optimization program of the computer. The Lumber Optimization Computer computes how the board 10 is to be cut and outputs the computed information into the Output Device 22. The Output Device 22 may either mark the board 10 where it is to be cut or alternatively cut the board where directed by the computer. As in the prior art system such as taught by Buss et al in patent 3,329,131, the cutting is limited to a cross cut which results in the basic pieces from which the desired pieces can be obtained by subsequent rip sawing to predetermined widths. The computed optimization information may also be used to generate an inventory on the number of pieces produced from the inspected board. This information may also update the priority of the individual pieces in the input order where priority is at least partially based on the number of pieces required. These latter procedures are well known and are not considered to be part of the invention and, therefore, will not be discussed in detail.

Figure 2:
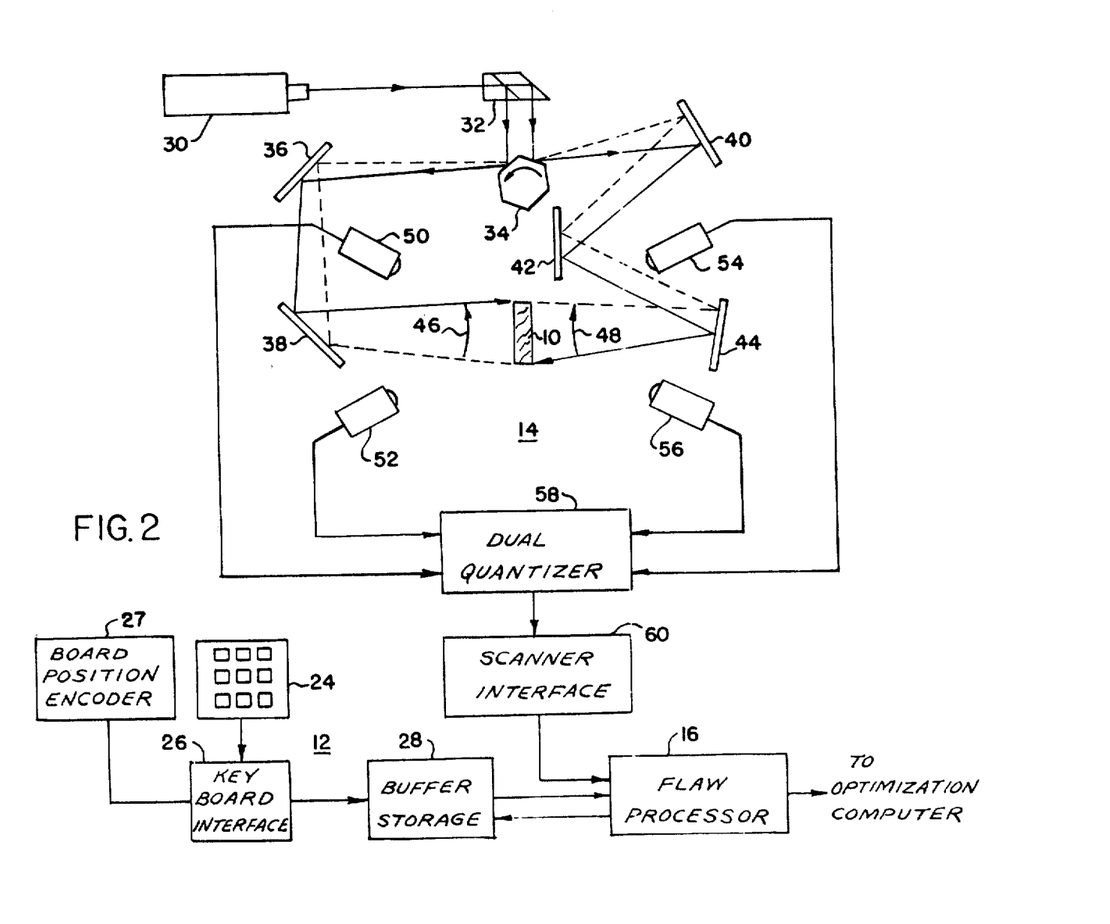
FIG. 2 is a block diagram illustrating the details of the electro-optical scanner and the flaw classification input devices.

The block diagram of FIG. 2 shows in greater detail individual elements of the Inspector Station 12 and the Electro-Optical Scanner 14. The Inspector Station 12 comprises an inspector defect classification control such as Keyboard 24, Keyboard Interface 26 and Board Position Encoder 27. The Board Position Encoder 27 generates encoded signals indicative of a distance measured from the boards leading edge as it is carried by the conveyor past a predetermined point in the Inspector Station. The Keyboard 24 has a plurality of keys by means of which the inspector serially designates the class of each flaw as it passes the same predetermined point in the Inspector Station. Data indicative of the flaw class from the Keyboard 24 and the signals from the Board Position Encoder 27 are combined in the Keyboard Interface 26 and placed in a format compatible with the computer language. The data from the Keyboard Interface 26 is temporarily stored in a Buffer Storage 28. The data stored in the Buffer Storage 28 is extracted by the Flaw Processor 16 and combined with the flaw data generated by the Electro-Optical Scanner 14 prior to optimizing the cutting of the board by the Optimization Computer 18.

In the following discussions involving electro-optical scanning, it will be assumed the board passes through the scanner in the Y direction and is line scanned in an X direction along the surfaces of the board normal to the Y direction. The Electro-Optical Scanner 14 comprises a Laser Light Source 30 generating a narrow beam of light. The generated light beam is divided into two spatially separated beams by a Beam Splitter 32 and caused to impinge upon a Rotating Multi Faceted Mirror 34. One beam is reflected by the Multi Faceted Mirror to scan the left side of the board 10 by means of a pair of fixed mirrors 36 and 38, the other beam is reflected by an alternate face of the rotating Multi Faceted Mirror to scan the opposite side of the board 10 by a second set of fixed mirrors 40, 42 and 44. The optical system is arranged to cause the two laser beams to alternately line scan opposite sides of the board along a line from bottom to top, as indicated by the arrows 46 and 48. Because the motion of the board through the scanner is continuous, the line scans on one side of the board interlace the line scans on the other side of the board. The portions of the laser beams reflected by the board are detected by two pair of photo detectors 50 and 52 and 54 and 56, one pair disposed on each side of the board, as shown to generate analog scan signals. Because the two sides of the board are alternately scanned, the line scan data from the opposite sides of the board are generated in an alternating sequence. The two photo detectors in each pair are angularly disposed to each other and to the surface of the board to maximize flaw detection. The analog signals from the two pairs of detectors are sequentially combined and processed by a Dual Quantizer 58. The Dual Quantizer 58 embodies a low frequency pass channel and a high frequency pass channel and means for converting the analog signals to digital form. The low frequency pass channel quantizes the scan data indicative of large flaws, such as knots, holes and the like. The high frequency pass channel quantizes the scan data indicative of narrow flaws, such as season checks and splits. The high frequency pass channel has additional digital filtering which simultaneously examines several scan lines and requires a repeated occurrence of a flaw along a line before transmitting high frequency pass flaw signals. This digital filtering suppresses spurious noise which may pass through the high frequency channel.

The signals from the Dual Quantizer 58 are accepted by the Scanner Interface 60 which encodes the position of the flaws within the line scan, whether the flaw appears on a low pass or high pass channel and whether the scan data was generated upon the occurrence of the scanning light beam entering or leaving a flaw area. In addition, the Scanner Interface separates the scan lines into scan frames and encodes the location of each flaw in the respective scan frame. The Scanner Interface also encodes other conditions, such as end of frame and end of board. This information is transmitted to the Flaw Processor 16 for further data manipulation.

Figure 3:
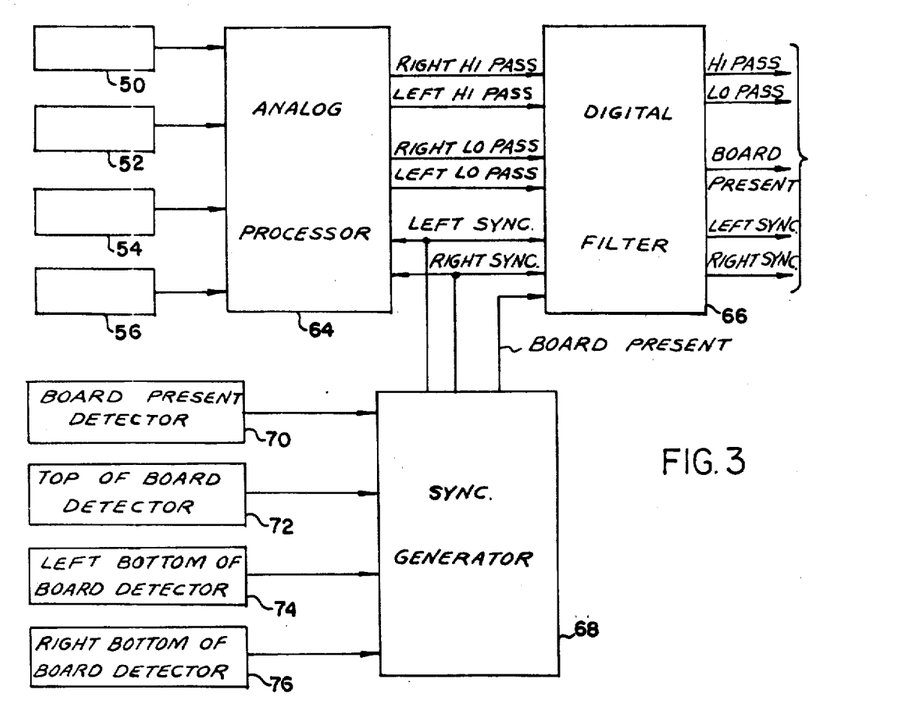
FIG. 3 is a block diagram of the dual quantizer.

The details of the Dual Quantizer 58 are shown in FIG. 3. The Dual Quantizers comprise an Analog Processor 64 receiving scan data from the Photo Detectors 50 through 56, a Digital Filter 66 and a Synchronization Generator 68 receiving signals from board associate sensors which shall be discussed later. The Analog Processor 64 provides amplification, serial combination of the scan data from the photo detectors, high and low pass frequency filtering, automatic gain control and quantization of the high and low frequency filtered scan data. The quantized high and low frequency scan data hereinafter referred to as "HI-PASS" and "LO-PASS" data from opposite sides of the board are transmitted to the Digital Filter for further processing.

The Synchronization Generator 68 receives signals from four independent sensors and provides various digital clocking, gating and counting functions. The Board Present Detector 70 generates a master gating signal permitting transmission of scan data to the Scanner Interface 60 only when a board is present in the Electro-Optical Scanner 14. Similarly, the Top of Board Detector 72, Left Bottom of Board Detector 74 and Right Bottom of Board Detector 76 are used to generate synchronization signals which gate data to the Scanner Interface 60 and Flaw Processor 16 only when the laser beam is impinging upon the surface of the lumber.

The Digital Filter 66 receives the quantized HI-PASS and LO-PASS scan data from the Analog Processor 64 which are clocked and gated by the synchronization signals from the Synchronization Generator 68. The HI-PASS data is processed through a special purpose digital filter to suppress noise and enhance the detection of splits and checks in the board. The filtered HI-PASS and LO-PASS data along with right and left synchronization signals and board present signals are processed in the Scanner Interface 60 which formats the data for subsequent processing in the Flaw Processor.

Figure 4:
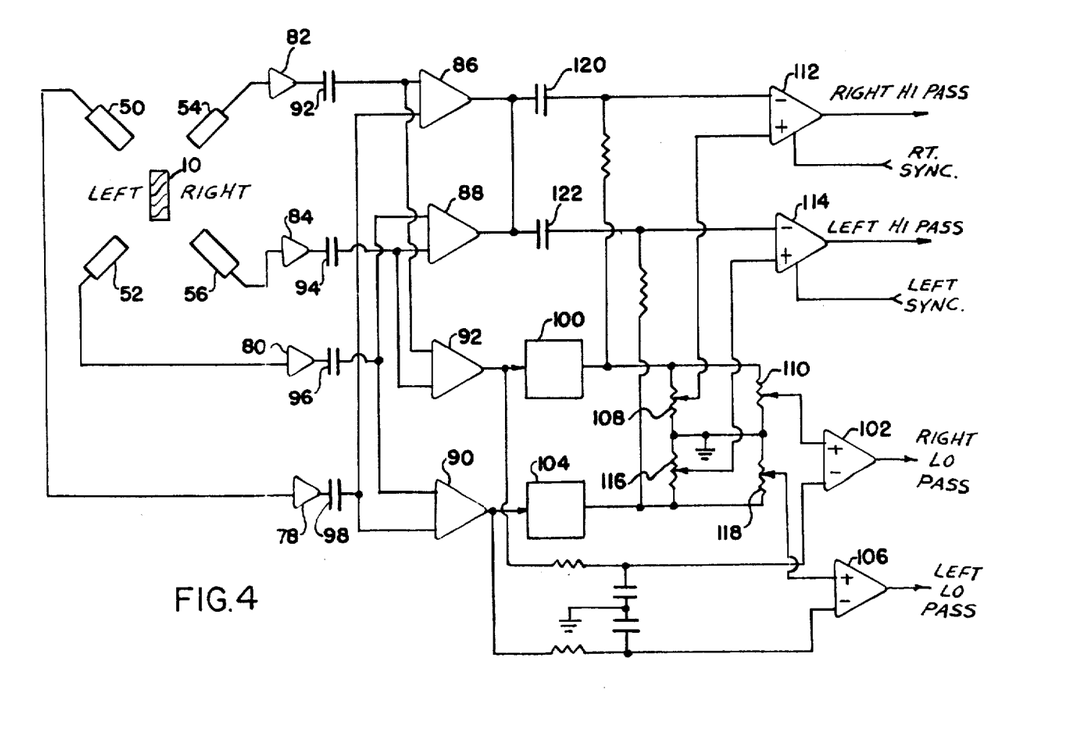
FIG. 4 is an electrical schematic of the analog processor.

The details of the Analog Processor 64 are illustrated in FIG. 4. Referring to FIG. 4, the analog signals from the four Photo Detectors 50 through 56 are amplified by associated preamplifiers 78, 80, 82 and 84. The amplified analog signals are capacitor coupled to upper HI-PASS filter 86, lower HI-PASS Filter 88, Left LO-PASS Filter 90 and Right LO-PASS Filter 92 by means of capacitors 92, 94, 96 and 98.

The output of the Right LO-PASS Filter 92 is transmitted to a Right LO-PASS Peak Holding Circuit 100 and the Right LO-PASS Comparator 102. The output of the Left LO-PASS Filter 90 is applied to Left LO-PASS Peak Holding Circuit 104 and Left LO-PASS Comparator 106. The output of the Right LO-PASS Peak Holding Circuit 100 is applied to a pair of Potentiometers 108 and 110. The opposite terminals of the two potentiometers are connected to ground. The wiper of Potentiometer 108 provides an AGC reference potential for the Right HI-PASS Amplifier 112. The wiper of Potentiometer 110 provides an AGC reference for the Right LO-PASS Comparator 102. The output of Right LO-PASS Peak Holding Circuit 100 is also applied to the negative terminal of the Comparator 112. The output of left LO-PASS Peak Holding Circuit 104 is applied to the input of comparator 114 and to pair of Potentiometers 116 and 118. The center tap of Potentiometer 118 provides an AGC referenced potential for Left LO-PASS Comparator 106 and the wiper of Potentiometer 116 provides an AGC reference potential for comparator 114. The output of Upper Photo Detector High Frequency Filter 86 and Low Photo Detector High Frequency Filter 88 are wire "OR'ed" to combine the signals from the Upper and Lower photo detectors and are capacitor coupled to Comparator 112 and 114 by means of Capacitors 120 and 122.

The operation of the Analog Processor 64 is as follows:

During the period when the laser beam is scanning the left surface of the board 10, the Photo Detector 50 generates an analog signal which is amplified by Preamplifier 78 and by means of Capacitor 98 is communicated to the Upper HI-PASS Filter 86 and to the Left LO-PASS Filter 90. In like manner, a Photo Detector 52 also generates a comparable analog signal which is amplified by Preamplifier 80 and is communicated to Lower HI-PASS Filter 88 and to Left LO-PASS Filter 90. The Left LO-PASS Filter removes the high frequency components of the analog signals from the detector and generates a LO-PASS signal which is a sum of the low frequency components of the two input analog signals. The LO-PASS signal is input into the Peak Holding Circuit 104 which generates a signal indicative of the peak intensity of the LO-PASS signal received from Detectors 50 and 52. The output signal from the Peak Holding Circuit 104 is applied to the negative input of the Comparator 114. This signal is also applied to Potentiometers 116 and 118 acting as signal dividers. The signal appearing at the wiper of potentiometer 116 is used as the AGC reference potential for Comparator 114. The signal at the center tap of Potentiometer 118 is used as the AGC reference potential input for the Left LO-PASS Comparator 106.

The high frequency components of the analog signal of Photo Detector 50 is passed through Filter 86 to remove the low frequency components of the analog signal. The high frequency (HI-PASS) output of the Filter 86 is communicated to the Left HI-PASS Comparator 114 by means of Capacitor 122. The HI-PASS signal generated is a negative signal which overcomes the bias potential of the Peak Holding Circuit 104 and causes Comparator 114 to produce a digitized HI-PASS signal. The left sync signal from the Sync Generator 68 gates Comparator 114 so that it is operative only when the left side of the board is being scanned. In a comparable manner, the analog signal from Detector 52 is applied through Preamplifier 80 and Capacitor 96 to the HI-PASS Filter 88 and the LO-PASS Filter 90. The high frequency components of the analog signal from Detector 52 is communicated to Comparator 114 through Lower HI-PASS Filter 88 and Capacitor 122. The low frequency component of the analog signal is passed by Filter 90 to Comparator 106 which generates a LO-PASS signal whenever the low frequency component is more negative than the bias potential produced at the wiper of Potentiometer 118. The operation of the Right HI-PASS and Right LO-PASS sections of the Analog Processor 64 are identical to the operation discussed with respect to Left HI-PASS and Left LO-PASS sections of the Analog Processor and need not be repeated for an understanding of the operation of the circuit.

Figure 5:
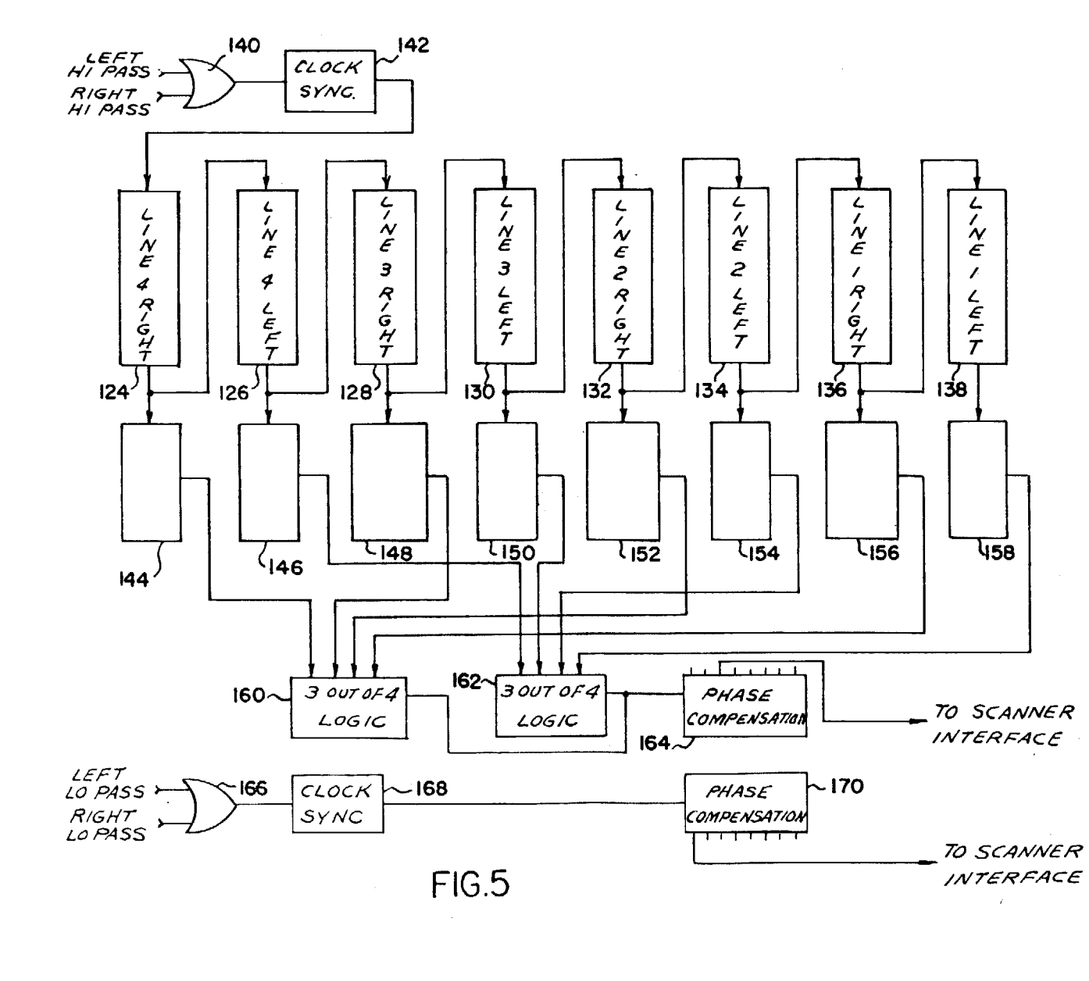
FIG. 5 is an electrical schematic of the digital filter.

The details of the Digital Filter 66 are illustrated in FIG. 5. The right and left HI-PASS signals from the Analog Processor 64 are alternately entered into a set of eight 256 bit Shift Register 124 through 138 by means of OR Gate 140 and Clock Synchronization Circuit 142 which converts the unclocked HI-PASS comparator data to clocked digital data. The eight shift registers are connected in series and each register holds exactly one scan line of digital HI-PASS data. Four consecutive scan lines from one side of the board are stored in four alternate shift registers 124, 128, 132 and 136 and four consecutive scan lines from the other side of the board are stored in the shift registers 126, 130, 134 and 138 in between the four registers storing the data from the opposite side of the board.

Eight Split Detector Circuits 144 through 158 observe the data pattern at the end of each 245 bit register and generate a signal when the data pattern at the end of the associated 256 bit register is indicative of a split. Three out of four Logic Circuits 160 and 162 receive signals from the alternating split detecotr circuits, as shown, and pass HI-PASS signals when at least three out of four associated split detector circuits are generating a signal indicative of a split. The output signal from the three out of four Logic Circuits 160 and 162 are input into a Phase Compensation Circuit 164 prior to being output to the Scanner Interface 60.

The right and left LO-PASS data are serially combined by OR Gate 166 and converted to digital form by Clock Synchronization Circuit 168. the digital LO-PASS data is input to a Phase Compensation Circuit 170 prior to being output to the Scanner Interface. The Phase Compensation Circuits 164 and 170 re-establish the proper phase relationship between the digital HI-PASS and LO-PASS data for subsequent manipulation in the Scanner Interface, Flaw Processor and Optimization Computer.

Figure 6:
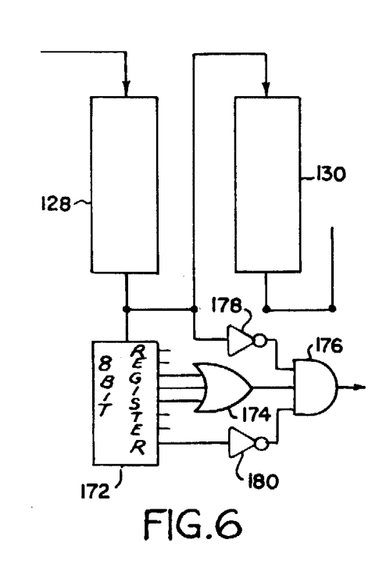
FIG. 6 is an electrical schematic of the split detector.

The details of the Split Detector Circuits 144 through 158 are illustrated in FIG. 6. Each Split Detector Circuit comprises an Eight Bit Register 172 holding the last eight bits of data in the associated 256 Bit Shift Register, as illustrated. An OR Gate 174 monitors the third, fourth and fifth data bits in the register 172 and outputs a signal when a high pass data bit is present in one or more of these three registers. The output of OR Gate 174 is input into an AND Gate 176 along with the outputs from inverter amplifiers 178 and 180. The Inverter Amplifiers 178 and 180 monitor the bit data disposed three bits on either side of the bits monitored by the OR Gate 174. If the output of OR Gate 174 indicates a flaw and simultaneously the outputs of Inverter Amplifiers 178 and 180 indicate no flaw, then a narrow defect is present. The output signal of AND Gate 176 is indicative that the defect is narrow, such as a crack, split or check.

Figure 7:
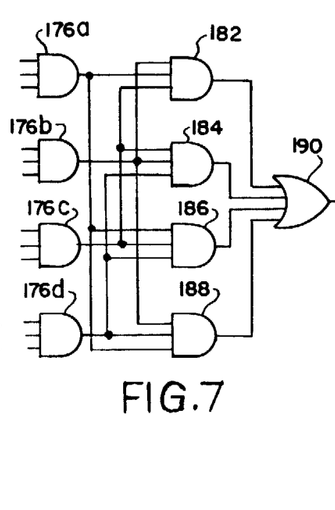
FIG. 7 is an electrical schematic of the three out of four logic.

The details of the three out of four Logic 160 and 162 are shown in FIG. 7. The outputs from the four AND Gates 176a through 176d associated with one side of a board are input to a like set of AND Gates 182 through 188. The first AND Gate 176a has its output connected to input gates of AND Gates 182, 186 and 188. The second AND Gate 176b has its output connected to inputs of AND Gates 182, 184 and 188 and, likewise, the two other AND Gates 176c and 176d have their outputs connected to input gates of three different AND Gates, as shown. The output of the AND Gates 182 through 188 are connected to inclusive OR Gate 190. The operation of the three out of four Logic is straight forward. When defect signals are present on all four AND Gates 176a through 176d, all of the AND Gates 182 through 188 output a defect signal and OR Gate 190 generates a signal indicative of a split or check. When only three of the four AND Gates 176a through 176d output a defect present signal, only one of the AND Gates 182 through 188 will output a defect signal to OR Gate 190. However, the OR Gate 190 will still generate a defect present signal. If more than one of the AND Gates 176 does not output a defect signal, then each of the AND Gates 182 through 188 has at least one no-defect signal at one of its input gates. A no-defect signal at an input of each of the AND Gates 182 through 188 inhibits the AND Gates and none produce a defect present signal. When none of the AND Gates have a defect present signal, OR Gate 190 will not produce a HI-PASS defect signal.

The Scanner Interface 60 formats the output data from the Dual Quantizer 58 in a form suitable for entry into the Flaw Processor 16. The specific functions of the Scanner Interface 60 are to generate specifically coded eight bit data bytes indicative of various occurrences during the scan processes and to subdivide the scan data into a plurality of discrete data frames to facilitate processing and reduce storage requirements for subsequent data manipulation in the Flaw Processor. Each data frame comprises the data from a predetermined number of scan lines which represent a predetermined section of the board having a specific length. The flaw data from the Scanner Interface is input to the Flaw Processor 16 on a frame-by-frame basis to permit flaw processing, such as analysis of the flaws and enlargement of the flaw area to proceed while scanning of subsequent sections of the board are still in progress.

The laser beam scans the board from bottom to top in a direction previously designated as the X axis and the board passes through the scanner along the Y axis. In accordance with this rationale, the Scanner Interface 60 generates X data bytes indicative of occurrences during the line scan along the X axis and Y data bytes at the end of each scan line and end of each frame and at the end of the board indicative of longitudinal data along the Y axis. Eight bit X data bytes are generated at each of the following occurrences:

Signal from the Dual Quantizer indicative that laser beam has entered a HI-PASS flaw region, signal from the Dual Quantizer indicative that laser beam has left a HI-PASS flaw region, signal from the Dual Quantizer indicative that laser beam has entered a LO-PASS flaw region, signal from the Dual Quantizer indicative that laser beam has left a LO-PASS flaw region, termination of the sync signals. Eight bit Y data bytes are generated at each of the following occurrences:

The end of each line scan line;

the end of each frame;

the end of the board.

Figure 8:
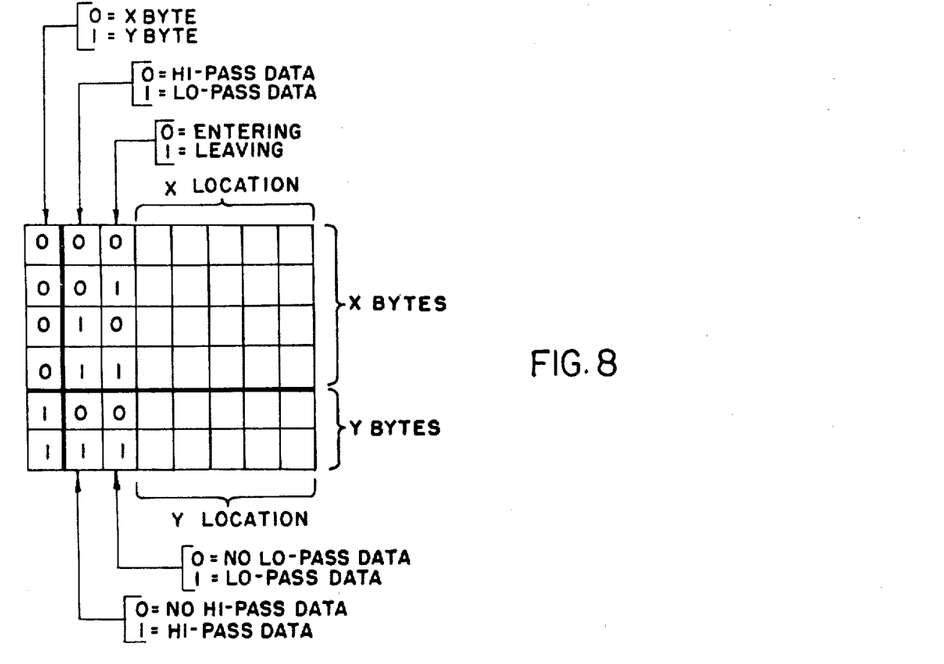
FIG. 8 illustrates the format of the X and Y data bytes.

The format of the eight bit X data bytes and those Y data bytes indicative of the end of a scan line are illustrated in FIG. 8. The first bit designates whether the data byte is an X byte or Y byte. A logic "0" is indicative of an X byte and a logic "1" is indicative of the Y byte. The second bit of an X byte designates whether the data is HI-PASS (logic 0) indicative of a check of split or LO-PASS (logic 1) indicative of a larger flaw, such as a knot or other defect. The third bit of the X byte designates whether the scanning beam is entering (logic 0) or leaving (logic 1) the flaw. The remaining five bits give the X location of the occurrence. The last LO-PASS entering X byte in each scan line is the top of the board byte.

The format of the Y byte is slightly different than that of the X byte. The second bit of the Y byte is indicative of the absence (logic 0) or presence (logic 1) of HI-PASS data during that entire scan line and the third bit of Y byte is indicative of the absence (logic 0) or presence (logic 1) of LO-PASS data during the entire scan line. The last five bits of the Y byte give the Y location of the scan line.

Figure 9:
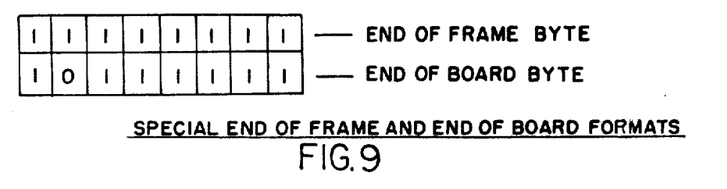
FIG. 9 illustrates the format of special Y data bytes.

The special formats illustrated in FIG. 9 are Y bytes indicative of the end of the frame and the end of the board.

The details of the Scanner Interface 60 are described with reference to the block diagram illustrated in FIG. 10. The board present and left (L sync) and right (R sync) signals from the Dual Quantizer are input to a Sync Processor 200 which generates counter enable, counter clear, and end of board signals for the X, Y and frame counters illustrated as block 202. The X computer counts clock pulses and generates five bit X locations for the X bytes, as a function of the position of the laser beam as it scans across the board in a direction approximately parallel to the X axis. The Y counter counts the sync signals and generates five bit location for the Y bytes indicative of the predetermined distance along the Y axis of the board within each frame. The frame counter is incremented by the Y counter after a predetermined number of scan lines have been counted. The five bit X and Y location signals are input directly into a Multiplexer 204 and the signal indicative of the end of a frame from the Y counter is input to a Fixed Code Generator 206 which generates the special code shown on FIG. 9 as indicative of the end of a frame. The Fixed Code Generator 206 also responds to the end of board (EOB) signal and generates the special code shown in FIG. 9 as indicative of the end of the board.

The digital HI-PASS and LO-PASS signals from the Dual Quantizer 58 along with sync signals from the Sync Processor 200 are input to Quantizer Processor 208 which generates the data bit indicative of whether the occurrence is from the HI-PASS or LO-PASS channel and whether the occurrence represents entering or leaving data, as required by the eight bit X byte format illustrated in FIG. 8. The data bits from the Quantizer Processor are also input to the Multiplexer 204 where it is combined with the appropriate location information generated by the X counter to produce an X byte.

The data bytes generated by the Multiplexer 204 are stored serially in a first-in-first-out (FIFO) Buffer 210. The purpose of this buffer is to temporarily store the data, if it is generated at a rate too fast to be read directly into the Flaw Processor 16.

The Scanner Interface 60 also includes an Address Generator 212 which generates memory addresses for the data bytes in the Flaw Processor and addresses for reading byte data from the FIFO Buffer 210 into a Duplexer 214. The Duplexer 214 alternately transmits sequential memory addresses from the Address Generator 212 and data bytes from the FIFO Buffer 210 to the Flaw Processor 16.

Figure 10:
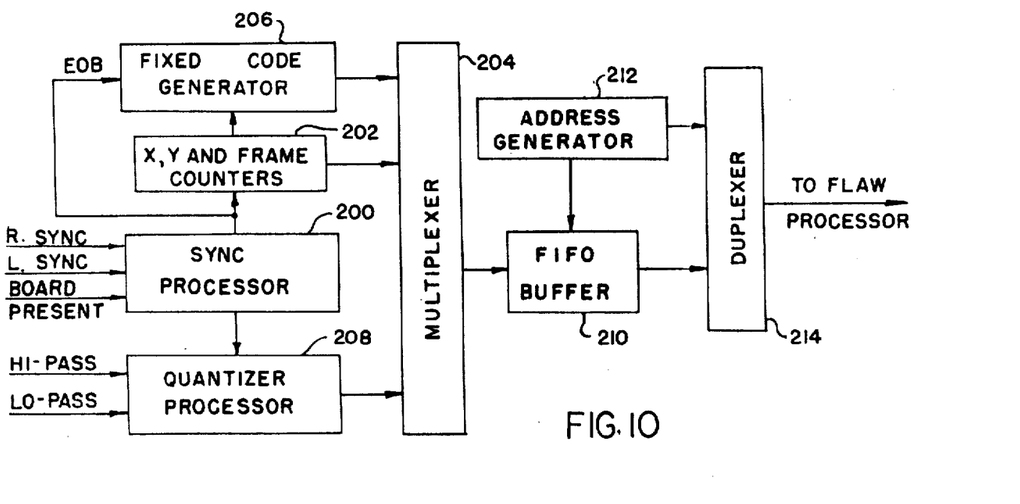
FIG. 10 is a block diagram of the scanner interface.

It is believed that circuits for performing the functions described with reference to the blocks in the block diagram illustrated in FIG. 10 are sufficiently well known and that detailed circuit diagrams are not required for a complete understanding of the Scanner Interface.

The Flaw Processor 16, as well as the Optimization Computer 18, may be individual hard wired or soft wired components having appropriate logic and storage capabilities or they may alternatively be embodied in a mini computer programmed to perform both desired functions. Because the mini computer option provides the maximum flexibility and adaptability to the many diverse applications for this type of a system, the preferred embodiment of the Flaw Processor 16 and Optimization Computer 18 is described in terms of a mini computer having the requisite storage facilities and programmed to perform both the flaw processing and optimization functions. A GTE IS-1000 manufactured by GTE Information Systems, Inc. of Fullerton, California has been used in the development of the Lumber Optimization system and is an example of one such mini computer capable of performing the desired functions.

Figure 11:
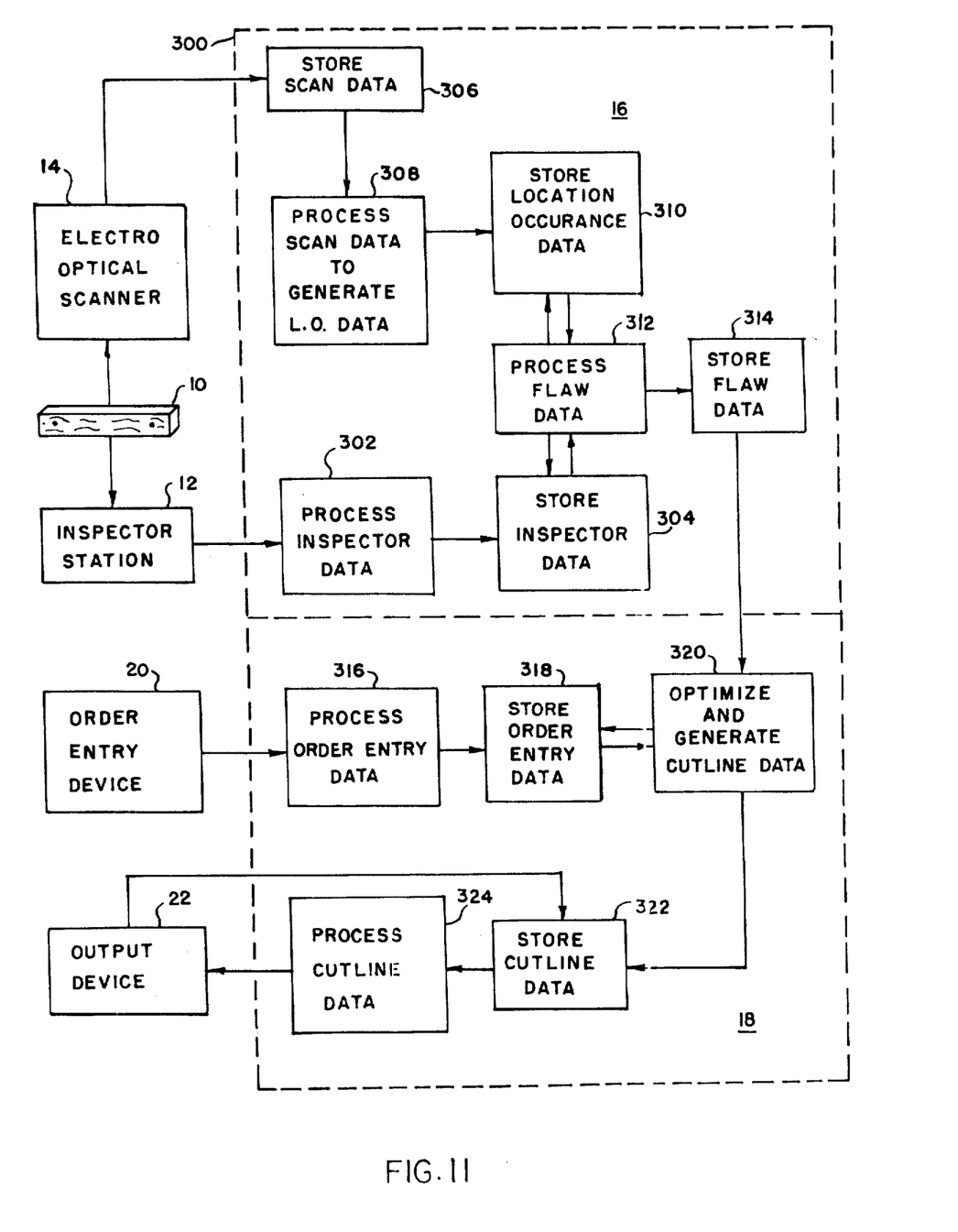
FIG. 11 is a block diagram illustrating the primary operational functions of the mini computer.

The block diagram (FIG. 11) shows the primary operational functions of the mini computer and its interrelationship to the external hardware. The board 10 first passes the Inspector Station 12 where a human inspector, by means of his keyboard, generates flaw class data indicative of the defect catagory of the flaws on the surface of the board in the order in which they will be detected by the Electro-Optical Scanner 14. The flaw class data generated at the Inspector Station 12 is processed in the computer block 302 and temporarily stored in the inspector data buffer, block 304. After passinfg through the Inspector Station, the board 10 passes through the Electro-Optical Scanner 14 which generates scan data in the form of X and Y bytes indicative of the size, shape and location of the flaws, as well as the special end of frame and end of board Y bytes. As previously discussed, the scan data from the Electro-Optical Scanner is temporarily stored in the mini computer in a Data Buffer on a frame-by-frame basis. Each frame of scan data in the Data Buffer is serially processed, block 308, to generate location occurrence data indicative of the location of the edges of the flaws and the location of the top of the board for each frame. The location occurrence (LO) data is temporarily stored in a location occurrence buffer, as indicated by block 310. The computer then generates flaw data by forming an enlarged rectangle about each flaw. The coordinates of the enlarged rectangle about each flaw are combined with the inspector flaw class data from block 304 and are tempoarily stored in a flaw buffer, as indicated by block 314. The order entry information is input to the computer through the Order Entry Device 20. The computer processes the order entry data, block 316, to form an order entry list, listing in the order of priority a description of each piece in the order. The order list is stored in an order list buffer indicated by block 318. The computer then optimizes the utilization of the board by comparing the sections of the board, as determined from the data contained in the flaw buffer with the type and size of boards desired from the order list buffer and generates cut line data indicative of where the board is to be cut to produce the optimum piece yield, as indicated by block 320. The cut line data indicative of the locations where the board is to be cut is stored in a cut line buffer, block 322, prior to being processed into a format useable by the Output Device. When the board is placed in the Output Device 22, the cut line buffer is interrogated and the cut line data is processed, as indicated by block 324, into a format acceptable by the Output Device 22 to either mark or cut a board in accordance with processed cut line data.

Figure 12:
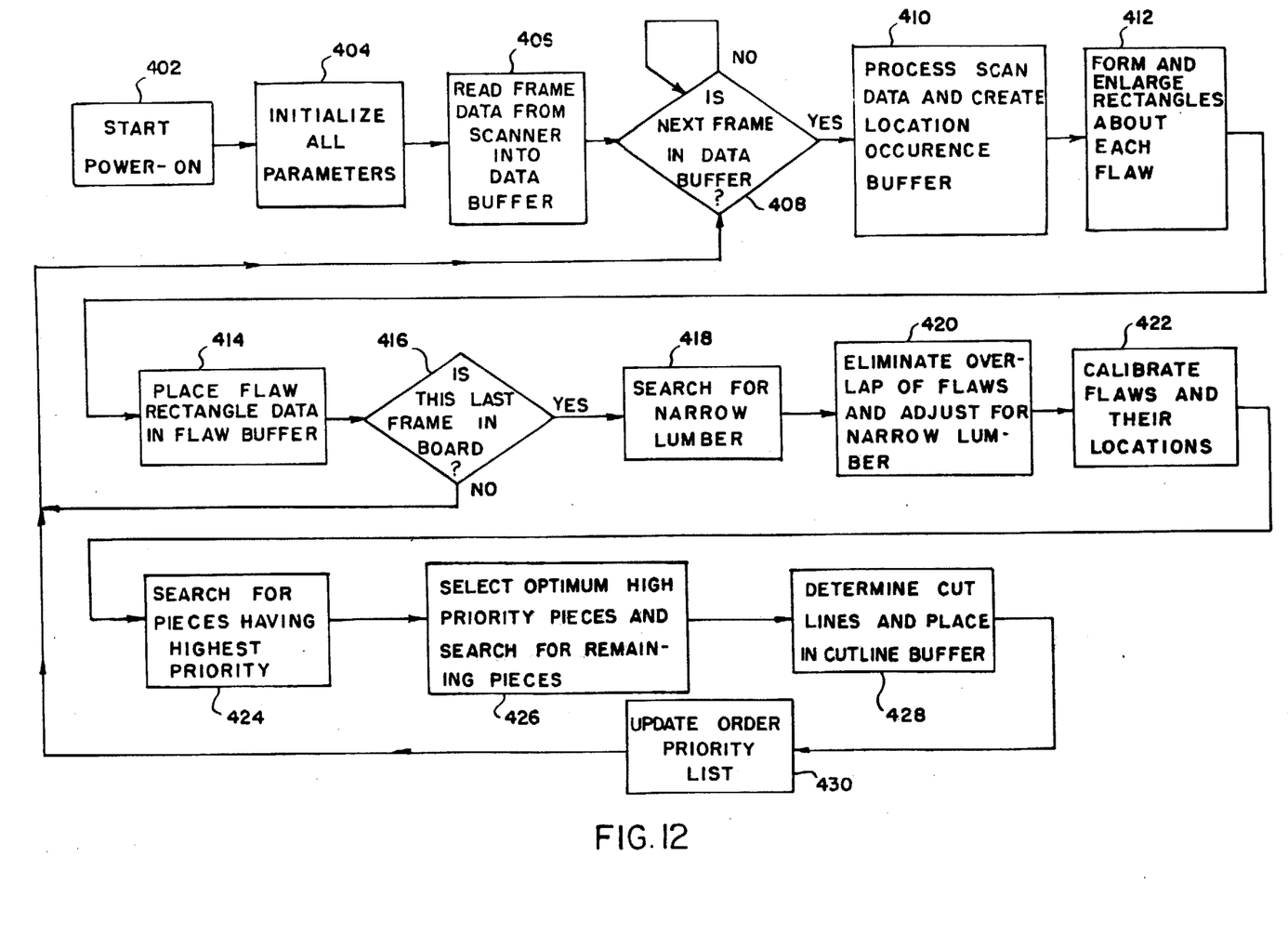
FIG. 12 is a flow diagram of the data in the mini computer.

A flow diagram of the computer program is shown in FIG. 12 while FIGS. 13, 14, 15, 16 and 17 illustrate the five interrupt subroutines of the computer program. Referring to FIG. 12, the program is initiated by turning on the system power, as indicated by block 402 which initializes all the system parameters, as indicated by block 404. In the initializing process, the input channel is started and the system is placed in a wait status until warmed up and ready to go. When the system is ready to go, a board is placed on the conveyor and the Electro-Optical Scanner begins to generate sequential frames of scan data, as previously discussed. Frames of scan data from the Electro-Optical Scanner are sequentially read into data buffer, as indicated by block 406. When a complete frame of data has been read into the data buffer, the scan data is processed, block 410, to create a location occurrence buffer. Each storage location in the location occurrence buffer corresponds to one of 32 locations of the X and Y data bytes. Each storage location acts as a counter. Whenever flaw data occurs at one of the 32 locations, the corresponding counter is incremented. Location occurrence buffers are formed for:

| Byte | Description |
|------|-------------|
| X | HI-PASS Entering |
| X | HI-PASS Leaving |
| X | LO-PASS Entering |
| X | LO-PASS Leaving |
| X | Top of Board |
| Y | HI-PASS Present |
| Y | LO-PASS Present |

The flaw processing portion of the program indicated by block 412 forms an enlarged rectangle about each flaw in accordance with a predetermined set of rules. For example, if the flaw is HI-PASS data indicative of a crack or a check, the flaw processing rule for this type of flaw may require that one inch be added to the beginning and to the end of the flaw data generated by the scanner and that the width of the flaw be increased by one tenth of an inch. However, if the flaw data is LO-PASS data, a different set of rules would apply. The enlargement rules for the LO-PASS data may also differ from one type of flaw to another depending upon whether the width of the flaw is greater than its height or vice versa. The difference in the way this data is handled is intended to eliminate during optimization various types of defects, such as cross grain, wood darkening and other defects which usually surround the larger flaws. There also may be other rules relative to the flaw processing based on whether the flaw occurs at the beginning or the end of the frame data, etc. These rules provide for continuity of a flaw which extends between two adjacent data frames. After the processing of the board is completed, the flaw data buffer contains the total number of flaws found along the whole length of the board. The last frame logic 416 responds to the Y byte data indicative of the end of the board and determines if the last frame entered into the flaw buffer is or is not the last frame of the board. If the frame is not the last frame of the board, then the next frame is entered into the location occurrence buffer 410. However, when a signal indicative of the end of the board is received, the optimization portion of a program is initiated. The first portion of the optimization program is the search for narrow number, as indicated by block 418. This process compares the top of board data for each frame and enters into the flaw buffer as a flaw, the missing portion of each frame which is narrower than a nominal width determined from the data in each frame. The next function of the optimization program is to eliminate the overlap of the flaws in the flaw buffer and adjust the program for the narrow lumber, as indicated by block 420. The next step, as indicated by block 422, is the calibration of the flaws and their locations on the board. The calibration process converts the location of the flaws and the dimensions of the board to conventional units of measure, such as inches in the English system or centimeters in the Metric system and also corrects for errors in the speed of the conveyor. After having calibrated the dimensions of the board and the precise location of the flaws along the length of the board in conventional units of measure, the optimization program 424 searches first for pieces in the stored order entry list having the highest priority. The program first selects pieces having the highest priorities and then searches for the pieces having lower priorities, as indicated in block 426. After the search has been completed, the cut lines are determined and data indicative of the cut line locations is placed in the cut line buffer, block 428. Having completed the optimization of the board, the program then checks for new entries to the priority list and updates, block 430, the order priority list prior to initiating processing data from the next board. After the priority list has been updated, a signal is generated to initiate processing data from a new board. The new board data should already be stored in the data buffer, as indicated by block 406.

Figure 13:
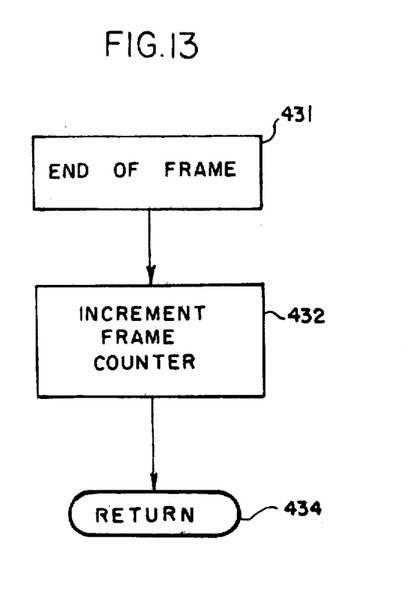
FIG. 13 is a flow diagram of the end of frame interrupt.

End of frame interrupt subroutine of FIG. 13 is executed at the end of each frame. The input channel access is enabled upon program start up and accepts scan data as the board passes through the scanner. The scan data is generated frame-by-frame and an interrupt 431 is produced at the end of each frame. The end of frame interrupt subroutine then increments a frame counter, resets the interrupt system to prepare for the next interrupt 432 and returns control 434 to the interrupted program. The program could be interrupted either during the processing of a previous frame of data while waiting for the interrupt, or during optimization of a previous board.

Figure 14:
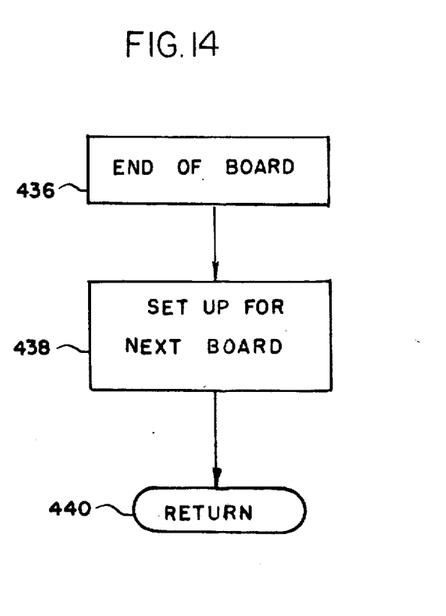
FIG. 14 is a flow diagram of the end of board interrupt.

The end of the board interrupt subroutine, FIG. 14 is executed at the end of the board. When the board leaves the scanner, an end of frame signal 436 is generated which increments a board counter, sets up the system 438 to receive data from a new board and returns the control 440 to the interrupted program.

Figure 15:
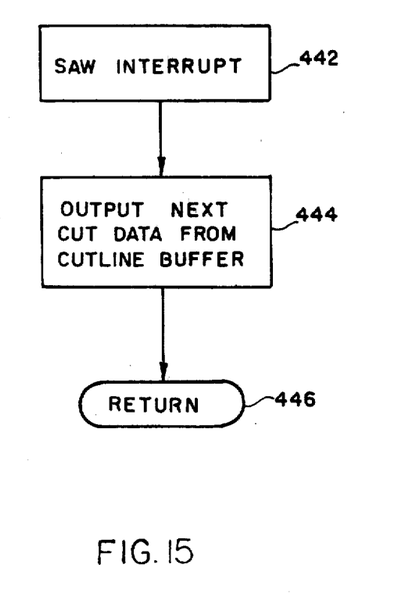
FIG. 15 is a flow diagram of the saw interrupt.
Figure 16:
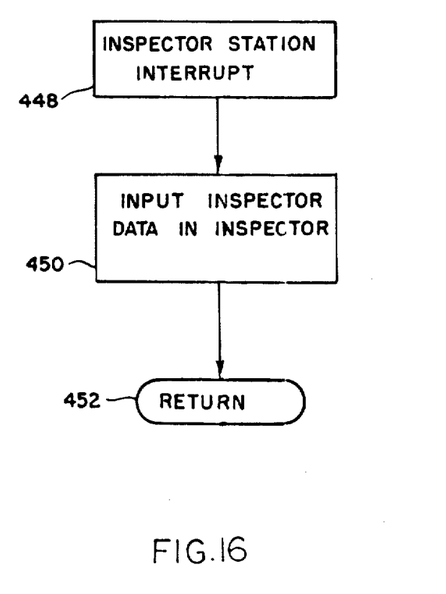
FIG. 16 is a flow diagram of the inspector station interrupt.

A saw interrupt 442 is generated when the pressure of a board is detected at the output device. The saw interrupt subroutine, FIG. 15, is then executed and outputs cut line data 444 to the output device 22 beginning at location zero. As each cut is made or marked, an additional interrupt is generated and new cut line data is output until no further cut line data is left in the cut line buffer. When the data in the cut line buffer is exhausted, the interrupt subroutine generates a return signal 446 indicative of finishing cutting. The next saw interrupt will then occur when the presence of a new board is detected at the output device.

The inspector station interrupt subroutine, FIG. 15, is executed each time the inspector enters the flaw class data by a means of his keyboard. The inspector station interrupt 448 inputs the data 450 from the Keyboard and Board Position Encoder into the inspector data buffer. When the flaw class data is entered, the subroutine returns control back to the program 452.

Figure 17:
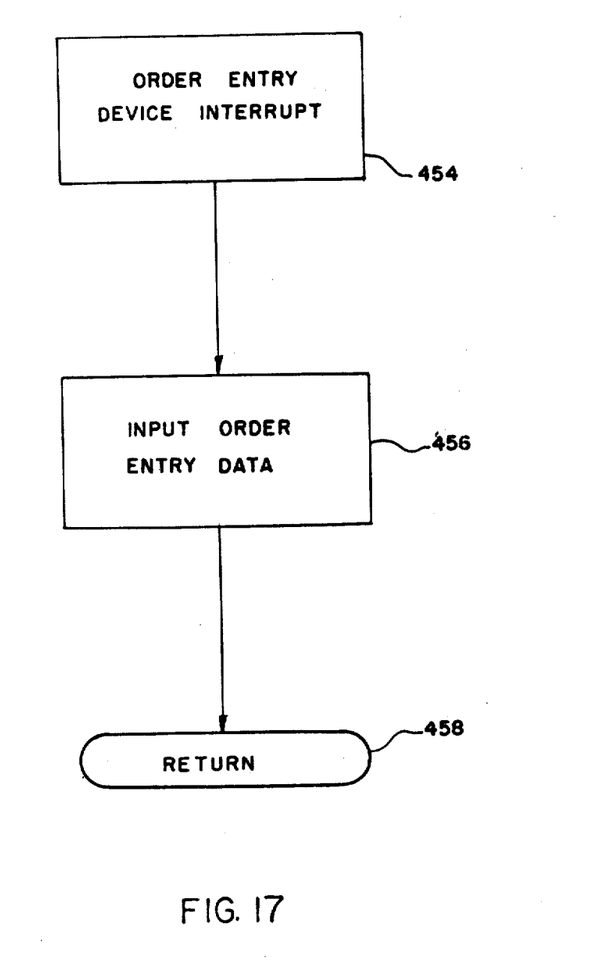
FIG. 17 is a flow diagram of the order entry device interrupt.

At the end of each optimization routine and prior to processing the data from the next board, the program executes an order entry interrupt, as shown on FIG. 17. The order entry interrupt 454 interrogates the order entry device and inputs 456 any new order entry data entered since the processing of the data from the prior board began updating the order priority list. When the order priority list is updated, the control is returned 458 to the program and processing of the data for a new board is initiated.

As indicated in the discussion of the prior art, programs for the inspection and optimizing the use of lumber are in existence both in printed publications and in issued patents. Since this information is readily available to those skilled in the art, it is believed that a further more detailed discussion of the optimization program is unnecessary for an understanding of the invention. The lumber inspection and optimization system has been described and illustrated with respect to a specific structure and specific program. It is not intended that the invention be limited to the scanning system illustrated and described, the coding format of the scanned data, nor the optimization program basically outlined. It is understood that those skilled in the art would be able to modify any one or all of these without departing from the spirit of the invention.

What is claimed is:

1. A system for optimizing the utilization of a board of lumber having flaws of irregular shapes and sizes which is to be cut into smaller pieces of predetermined dimensions comprising:

conveyor means for moving said board in a predetermined direction at a predetermined constant speed;

means disposed along the path of said conveyor means for line scanning at a predetermined frequency the surfaces of said board in a direction normal to said predetermined direction of motion to generate analog scan data having frequency components indicative of the characteristics of surfaces being scanned, said means further including means for generating a board present signal when a board is present in said means for line scanning;

quantizer means having frequency filtering means for generating HI-PASS and LO-PASS digital scan data quantized with respect to the frequency components of said analog scan data, said HI-PASS digital scan data indicative of long narrow flaws generated in response to analog scan data having a frequency component higher than a predetermined frequency, and said LO-PASS digital scan data indicative of larger flaws including the edge of the board generated in response to analog scan data having frequency components lower than said predetermined frequency, said quantizer means further including means for generating sync signals in synchronization with said line scans;

scanner interface means receiving said HI-PASS and LO-PASS digital scan data, said sync signals and said board present signal for encoding said HI-PASS and LO-PASS digital scan data in a predetermined format;

means for generating order entry data indicative of the dimensions, permitted flaws and priority of the pieces to be cut from said board in response to an input from an external source;

computer means having sufficient storage and computation means for selecting from said board, in a descending order of priority, pieces having no or only permitted flaws and for generating cut line data indicative of the end locations of said selected pieces, said computer having means for receiving and storing said HI-PASS and LO-PASS digital scan data encoded in said predetermined format means for receiving and storing said order entry data, means for generating a flaw data buffer storing the dimensions of the board and the location of the edges of the flaws determined from said encoded digital scan data, means for processing and said order entry data in a descending order of priority, means for selecting pieces having no or only permitted flaws from said board in said descending order of piece priority and means for generating said cut line data; and means disposed along said conveyor to receive said board after passing through means for line scanning for operating on said board in response to said cut line data.

2. The system of claim 1 wherein said means for operating is a marker for placing on said board marks indicative of the location where the board is to be cut.

3. The system of claim 1 wherein said means for operating is a saw means for cutting said lumber at the locations indicated by said cut line data.

4. The system of claim 1 wherein said quantizer means comprises:

synchronization means for generating said sync signal indicative of the beginning and end of each line scan across each surface of the board;

analog processor means separating the high frequency components of said analog scan data from said low frequency components for quantizing means including a clock generating clock signals for digitizing said HI-PASS and LO-PASS quantized data to generate said HI-PASS and LO-PASS digital scan data.

5. The system of claim 4 wherein said quantizer means further includes a digital HI-PASS filter means for detecting the repeated occurrence of said HI-PASS digital scan data in a plurality of sequential line scans for suppressing spurious high frequency noise.

6. The system of claim 1 wherein said scanner interface means comprises:

quantizer processor means for processing said HI-PASS and LO-PASS digital scan data to generate HI-PASS/LO-PASS binary bit data indicative of whether said digital scan data is HI-PASS digital scan data or LO-PASS digital scan data respectively and ENTERING/LEAVING binary bit data indicative of whether said HI-PASS and LO-PASS digital scan data is entering or leaving a flaw area;

sync processor means for processing said sync signals to generate a first signal indicative of the beginning of a scan line, said sync processor further including means for generating an end of board signal upon the termination of said board present signal;

X counter means including an X counter clock generating X clock signals at predetermined intervals, said counter enabled by said first signal and said lumber present signal for generating binary numbers indicative of X locations at periodic intervals determined by said X clock signals;

Y counter means responsive to said sync signals for generating binary numbers indicative of Y locations for each scan line said Y locations indicative of predetermined distances along the surface of said lumber in the direction of lumber motion;

frame counter means counting said sync signals for generating an end of frame signal after counting a predetermined number of sync signals;

fixed code generator means for generating an end of frame code signal in response to receiving an end of frame signal and an end of board code signal in response to receiving an end of board signal;

multiplexer means receiving said HI-PASS/LO-PASS bit data, said ENTERING/LEAVING bit data, said binary number indicative of X and Y locations and said end of frame and end of board code signals for generating multi bit X and Y bytes of digital data, said multiplexer means generating said X bytes of digital data upon the receipt of data indicative of the line scan entering or leaving a flaw area, including leaving the edge of the board, said X byte including a binary bit identifying the byte as an X byte a binary bit identifying whether the data is HI-PASS or LO-PASS data a binary bit identifying whether the line scan is entering or leaving the flaw area and the binary number indicative of the X location, said multiplexer mean further generating multi bit Y bytes at the end of each line scan, at the end of frame and at the end of board, said Y byte including a binary bit identifying the byte as a Y byte, bits indicating the presence or absence of HI-PASS and LO-PASS data during the particular line scan and the binary number indicative of the Y location of said line scan and said Y bytes indicative of the end of the frame and end of the board having data bit codes generated by said fixed code generator;

first-in-first-out buffer means for temporarily storing said X and Y byte data in the order in which they are generated;

address generator means generating memory addresses and signal for serially extracting the X and Y byte data from said first-in-first-out buffer means; and duplexer means for serially combining the memory addresses with the X and Y bytes data to generate said encoded data.

7. The system of claim 6 wherein said order entry data further includes at least one piece having a permitted class of flaw on at least one surface, said system further includes:

an inspector station upstream of said means for line scanning, said inspector station having a flaw class entry means for generating flaw class data indicative of the flaw location and flaw class in response to inputs from the human inspector; and said computer means further includes means for combining said flaw class data with the associated flaw data stored in the flaw data buffer.

8. A method for optimizing the utilization of a board of lumber having flaws of irregular sizes and shapes which is to be cut into pieces of predetermined dimensions comprising the steps of:

moving the board in a predetermined direction at a determinable speed through an electrooptical scanning device;

line scanning at least one surface of said board in a direction normal to said predetermined direction of motion to generate analog scan data having frequency components, said frequency components indicative of the surface characteristics of said at least one surface;

generating sync signals synchronous with said line scans;

generating a board present signal when a board is present in said optical scanning device;

filtering the frequency components of said analog scan data to separate the high frequency components from the low frequency components;

quantizing said high frequency and low frequency components to generate HI-PASS and LO-PASS data respectively, said quantized HI-PASS data indicative of long narrow flaws and said quantized LO-PASS data indicative of larger flaws including the edge of the board in the direction of the line scan;

gating said quantized HI-PASS and LO-PASS data at a predetermined frequency to generate digital HI-PASS and digital LO-PASS data;

digitally filtering a plurality of adjacent line scans of digital HI-PASS data to remove non-repetitive HI-PASS data;

processing said digital HI-PASS and LO-PASS data to generate a first bit of binary data having a first logic state indicative of HI-PASS data and a second logic state indicative of LO-PASS data and to generate a second bit of binary data having a first logic state indicative of the occurrence of a line scan entering a flaw area and a second logic state indicative of an occurrence of said line scan leaving a flaw area;

activating binary counters with said sync signals and said board present signal to generate binary numbers indicative of the X location of the line scan on the board in a direction normal to said predetermined direction of motion, to generate binary numbers indicative of the Y location of the line scan on said board along said predetermined direction of motion, to generate end of frame signals at the completion of a predetermined number of line scans and to generate an end of board signal in response to the termination of said board present signal;

generating an end of frame code signal in response to said end of frame signal and end of board code signal in response to said end of board signal;

multiplexing said first bit of binary data, said second bit of binary data, said binary numbers indicative of X and Y locations and said end of frame and end of board code signals to serially generate in their order of occurrence X byte data indicative of the location of the edges of the flaws and the top of the board in the direction of the line scan and Y byte data indicative of the location of the scan line within a frame, the end of each frame and the end of the board in a direction parallel to said predetermined direction of motion;

entering into an order entry device piece information indicative of the dimensions and priority of pieces desired to be cut from the board to generate an order entry list storing said piece information in a descending order of priority;

processing said X and Y byte data to generate a flaw data buffer storing in predetermined storage locations data indicative of the location of the top of the board and the location of the edges of rectangles circumscribing each flaw; and selecting pieces having no flaws from said board in their descending order of priority of said entry order list to generate cut line data indicative of the end location of said selected pieces.

9. The method of claim 8 further including the steps of:

placing the board in a marking device; and marking said board in response to said cut line data at the generated cut line locations.

10. The method of claim 8 further including the steps of:
   placing the board in an automatic sawing device, and sawing said board in response to said cut line data at the generated cut line locations.

11. The method of claim 8 wherein said step of line scanning further includes the step of alternately line scanning a surface of said board opposite said at least one surface in a direction normal to said predetermined direction of motion to sequentially generate analog scan data indicative of the surface characteristics of both surfaces.

12. The method of claim 8 wherein said step of processing said X and Y bytes data comprises:
   temporarily storing said X and Y byte data on a frame-by-frame basis;
   decoding said X and Y byte data frame-by-frame to form a location occurrence buffer temporarily storing in predetermined storage locations data indicative of the location of the top of the board and said data indicative of the location of the edges of a rectangle circumscribing each flaw;
   forming enlarged rectangles in accordance with predetermined rules about each flaw in the location occurrence buffer to form said flaw data buffer, said flaw data buffer storing the edge locations of the enlarged rectangles;
   comparing the data indicative of the top of the board stored in the location of occurrence buffer with nominal locations for the top of the board to generate top of board flaw data, and storing said top of board flaw data in said flaw data buffer.

13. The method of claim 12 wherein said step of selecting pieces comprises:
   comparing the location of the edge locations of the enlarged rectangles formed about adjacent flaws to consolidate overlapping flaw data;
   converting the edge locations of the enlarged rectangles and the data indicative of the top of the board from computer units of measure to conventional units of measure;
   searching through the flaw data buffer to identify and select high priority pieces that may be taken from the board then searching the remaining portion of the board and selecting therefrom other pieces in their order of priority until the order entry list is exhausted; and
   storing the end locations of said selected pieces to generate said cut line data.

14. The method of claim 11 wherein said entry data includes data indicative of at least one class of flaw permitted in at least one piece to be cut from the board, said method further includes:
   generating flaw class data indicative of the classification and approximate location of the flaws on the surfaces of the board in response to inputs to a defect classification device by a human inspector;
   and said step of processing said X and Y byte data further includes the step of storing said flaw class data to form an inspector data buffer;
   and said included step of forming enlarged rectangles further includes the step of combining said flaw class data with the data stored in the location occurrence buffer to generate a flaw data buffer including both the edge locations of the enlarged rectangles and said flaw class data.

* * * * *